United States Patent [19]
Teo et al.

[11] Patent Number: 5,885,218
[45] Date of Patent: Mar. 23, 1999

[54] METHOD AND APPARATUS FOR SPATIAL FILTERING IN AN INTRAVASCULAR ULTRASOUND IMAGING SYSTEM

[75] Inventors: Tat-Jin Teo, Sunnyvale; J. Steve Reynolds, Fremont, both of Calif.

[73] Assignees: SciMed Life Systems, Inc., Maple Grove, Minn.; Boston Scientific Limited, Barbados

[21] Appl. No.: 966,395

[22] Filed: Nov. 7, 1997

[51] Int. Cl.[6] .................................................. A61B 8/00
[52] U.S. Cl. ............................................................ 600/443
[58] Field of Search .................................. 600/443, 447, 600/454, 455, 916

[56] References Cited

U.S. PATENT DOCUMENTS

| | | | |
|---|---|---|---|
| 5,476,096 | 12/1995 | Olstad et al. | 128/660.07 |
| 5,503,153 | 4/1996 | Liu et al. | 73/861.25 |
| 5,538,004 | 7/1996 | Bamber | 128/916 X |
| 5,568,811 | 10/1996 | Olstad | 600/443 |
| 5,582,173 | 12/1996 | Li | 600/443 |
| 5,623,929 | 4/1997 | Weng | 600/455 |
| 5,655,535 | 8/1997 | Friemel et al. | 128/916 X |

OTHER PUBLICATIONS

Maragos, Petros, "Morphological Correlation and Mean Absolute Error Criteria," *IEEE*, 1989, pp. 1568–1571.

Barnea, Daniel I. and Silverman, Harvey F., "A Class of Algorithms for Fast Digital Image Registration," *IEEE Transactions on Computers*, vol. C–21, No. 2, Feb. 1972, pp. 179–186.

*Primary Examiner*—Francis J. Jaworski
*Attorney, Agent, or Firm*—Townsend and Townsend and Crew

[57] ABSTRACT

A spatial filtering method and apparatus which is particularly useful for addressing the problem of pulsation motion in intravascular ultrasound imaging, but may also be applied to imaging systems in other environments. According to a specific embodiment, the present invention provides a method and related apparatus for determining relative motion (rotation, pulsation, or in-plane translation and/or a combination thereof) in orthogonal r-θ memory space, prior to scan conversion, between a first and second image frame, and displaying an accurate image and/or performing pre-scan conversion image stabilization of the image.

22 Claims, 8 Drawing Sheets

METHOD AND APPARATUS FOR SPATIAL FILTERING IN AN INTRAVASCULAR ULTRASOUND IMAGING SYSTEM

BACKGROUND OF THE INVENTION

The present invention relates to high resolution intravascular imaging and more particularly to ultrasound imaging and techniques for efficient and accurate image processing needed for enhanced image display.

In some types of intraluminal or intravascular ultrasound (also referred to as "IVUS") systems, an ultrasonic unidirectional exciter/detector within a catheter probe positioned within a blood vessel is used to acquire signal data from echoes of the emitted ultrasonic energy off the interior of the blood vessel. In intraluminal ultrasound imaging, the production of high resolution images of vessel wall structures requires imaging at high ultrasound frequencies. Vectors are created by directing focused ultrasonic pressure waves radially from a transducer in a catheter and collecting echoes at the same transducer from the target area. A plurality of radial vectors from the rotated transducer comprises an image frame. A signal processor performs image processing on the acquired data in order to provide a display of the intravascular image on a raster-scan display monitor. As the intravascular image displayed is used by doctors or other skilled technicians in examining the interior of the blood vessel in order to facilitate accurate diagnoses and/or to perform intricate medical procedures, it is important that the displayed image be as stable and accurate as possible and comfortably viewed. However, the movements of and within the blood vessel due to systolic and diastolic movement of the heart cause the displayed images to move on a frame-by-frame basis, thereby resulting in an unsteady view of the intravascular region. The occurrence of these movements complicates the signal processing required to provide a stable and accurate intravascular image display. Determining on a frame-by-frame basis whether and how much the image has moved is important for accurate image display or so that the image in successive frames can be accordingly adjusted to compensate for that motion.

In intravascular ultrasound imaging, three types of frequently encountered relative motions between the catheter and the blood vessel need to be analyzed: pulsation, rotation, and in-plane translation. These motions are described in the context of a plane that is in transverse cross-section to the blood vessel through which blood normally flows along the length of the blood vessel. Specifically, pulsation involves the inward and outward radial motion, uniformly or non-uniformly, of the blood vessel and blood region. Rotation involves the turning of the blood vessel and blood region with respect to the location of the center of the blood vessel. In-plane translation involves the movement within the plane of the blood vessel and blood region. Of course, some combination of these three types of motions is often encountered in intravascular ultrasound imaging and must be efficiently analyzed to provide an accurate and/or stable image display.

The problem of image displacement can be a complex matter in intravascular imaging systems, greatly affecting the quality and accuracy of the image displayed. The quality and accuracy of the displayed image is very important for doctors who may be performing intricate and often life-dependent procedures based on their real-time observations and reactions to the displayed image. For example, when the heartbeat causes blood vessels to pulsate and move in a complex manner, conventional imaging systems will show this rapid motion, making it extremely difficult for doctors to view and determine what is going on within the vessel. It is therefore very important to determine the type and quantity of the motion encountered so that an accurate image display may be provided. In addition, the image may be moved and adjusted to compensate for these motions and thereby stabilize the displayed image. It is desirable in some applications that the displayed image is sufficiently stabilized on a frame-by-frame basis with image processing analysis after data acquisition. Once the image is stabilized, then temporal filtering for blood speckle and other image enhancement techniques may be performed by existing means and techniques in order to view a corrected and filtered image.

Figure 1:
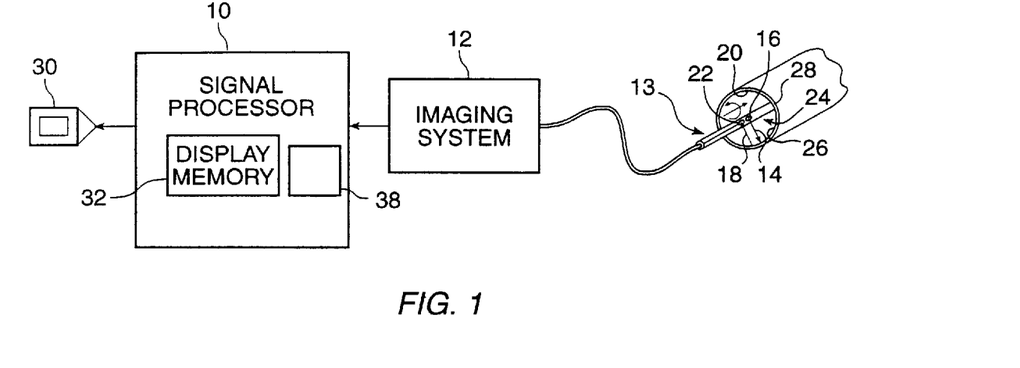
FIG. 1 is a block diagram of an intravascular ultrasonic imaging system in accordance with the invention.

FIG. 1 illustrates such a conventional ultrasonic imaging system that may be used for intravascular image display. As seen in FIG. 1, a specialized signal processing device 10 is used with an ultrasonic imaging system 12 including a catheter probe 13 wherein ultrasonic beams 14 are emitted by an ultrasonic transmitter or exciter 16. The ultrasonic imaging system of FIG. 1 performs data acquisition for the intravascular image in polar coordinates (r, θ). Radial spokes or vectors 18 of information are collected from a target 20 (the interior walls of a blood vessel) based on ultrasonic reflections at a transducer 22. Specifically, information is gathered by projecting narrow ultrasonic sampling beams 14 from exciter 16 as it is rotated (by an angle θ) within catheter 13 within blood vessel 20. The reflections scale in amplitude over a range and are recorded by transducer 22 as amplitude as a function of unit distance (r) along the radius of each vector. The image is representative of a cross-sectional "slice" of the structure of blood vessel 20 and includes wall structures (bloodwall interface) 26 and lumens of blood (blood region) 24, as seen in FIG. 1. This image data may be originally acquired as either analog or digital information, depending on the specific system utilized.

The data acquired is converted into pixels representing points in a scanned (swept or rotated) two-dimensional image. The pixels are assigned a value on, for example, a gray scale between black and white. Of course, in other embodiments, the assigned value may be on a color scale. After the conventional intravascular ultrasonic imaging system acquires the image data, signal processor 10 scan-converts the acquired image data and then stabilizes the rasterized scan-converted image data on a frame-by-frame basis, and then provides the raster image for viewing on a display device 30 coupled to signal processor 10. Scan conversion involves converting the digitized acquired image data into x-y rasterized image data for storing into the display memory 32 within signal processor 10. Scan conversion of data acquired in polar coordinates (r, θ) to pixels represented in rectangular coordinates (x, y) involves a translation (x=rcosθ and y=rsinθ) in the purely mathematical domain. Thus, each sample point acquired in polar coordinates may or may not coincide with a pixel in rectangular coordinates. Therefore, interpolation between polar coordinate sample points is often required in order to obtain each pixel in the x-y raster image. Moreover, it is apparent that some of the originally acquired data is lost upon performance of the scan conversion due to the resolution of the interpolation being insufficient to make the "polar data acquisition"-to-"rectangular scan conversion" translation transparent. Accordingly, as scan conversion quality varies, conventional intravascular ultrasonic imaging systems which provide scan-converted x-y raster image display from data acquired in polar coordinates thus may result in less accurate data representation due to the interpolation required.

Subsequent to scan-conversion (and the A/D conversion for analog acquired data), a signal processor used with conventional intravascular ultrasound imaging systems performs image processing analysis by correlation techniques on the scan-converted x-y image data in order to provide a stabilized image on a frame-by-frame basis, as discussed earlier. Examples of such correlation techniques are discussed in detail by Daniel I. Barnea and Harvey F. Silverman in an article entitled "A Class of Algorithms for Fast Digital Image Registration," on pages 179–186 of the *IEEE Transactions on Computers*, Vol. C-21, No. 2, February 1972, and by Petros Maragos in an article entitled "Morphological Correlation and Mean Absolute Error Criteria," on pages 1568–1571 of the *IEEE Proceedings* 1989 *of the International Conference on Acoustic Speech and Signal Processing*. Both articles are herein incorporated by reference for all purposes.

Using such correlation techniques on scan-converted x-y image data, the conventional signal processor in intravascular ultrasound systems compares successive image frames to determine what type and how much motion has occurred so that the second image frame can be re-registered with the first image frame and a corrected image can be displayed. In particular, a "region of interest" or "window" of the image frame is selected, the region of interest is compared to a "search region" larger than the region of interest, and the region of interest is moved through all possible steps in the search region to locate a specific location in the search region where there is a maximum correlation (as great as 1) with the region of interest. The position of the correlation peaks is used to determine how the image has moved. Thus, the type and quantity of the frame-by-frame motion of the image can be determined, and the second image can be re-registered to that location in the first image to thereby adjust or correct the displayed image to compensate for the motion.

In the specific imaging environment in intravascular ultrasound systems, the conventional region of interest has been rectangular (e.g., square), primarily because the various motions can be analyzed satisfactorily in rectangular (x, y) coordinates. In particular, post-scan conversion image processing analysis using the conventional rectangular region of interest in the x-y coordinate domain is able to easily handle in-plane translation by breaking down the motion into its x-component and y-component. Rotational motion using the conventional rectangular region of interest in the x-y coordinate domain is also fairly easily handled by using the arctangent function. However, pulsation is difficult and complex to analyze, as it violates the rigid body motion which conventional image processing analysis assumes. Accordingly, conventional systems with post-scan conversion image processing analysis using a rectangular region of interest must compensate for the non-rigid body motion encountered in pulsation by using computations which may result in an image display with limited accuracy. For example, the rectangular region of interest may be broken into multiple (e.g., four) rectangular sub-regions of interest within the larger region of interest and image processing performed for each rectangular sub-region of interest. The respective motions of each rectangular sub-region of interest relative to each other are used to determine how much pulsation occurred in a crude manner. Conventional intravascular ultrasound image processing systems thus may be limited to displaying a poor or inaccurate representation of the intravascular image, particularly when encountering motion such as pulsation.

From the above, it can be seen that improved methods and apparatus are needed to provide more accurate and/or stable images for display in ultrasonic intravascular imaging systems.

SUMMARY OF THE INVENTION

The method and apparatus of the present invention provide images with better accuracy than conventional methods and apparatus. Specifically, the present invention provides a spatial filtering method and apparatus which is particularly useful for addressing the problem of accurate imaging when encountering motions such as pulsation, rotation, or in-plane translation, or some combination thereof in intravascular ultrasound imaging, but may also be applied to imaging systems in other environments.

According to a specific embodiment, the present invention provides a method of determining relative motion between successive intravascular ultrasound blood vessel images. The method includes the steps of illuminating an intravascular target with ultrasonic energy to generate ultrasonic echoes from an intravascular target, and transforming the ultrasonic echoes from the intravascular target into a received signal to acquire first image data in polar r-θ coordinates for a first image frame of an intravascular ultrasound blood vessel image and second image data in polar r-θ coordinates for a second image frame of the intravascular ultrasound blood vessel image. The second image frame and the first image frame are successive image frames. The method also includes the step of comparing, prior to scan conversion, the first image data and the second image data to determine the type and quantity of relative motion from the first image frame to the second image frame. In other specific embodiments, the method also includes the steps of performing, prior to scan conversion, an image stabilization analysis between the second image data and the first image data in the orthogonal r-θ memory space by using a rectangular region of interest in the second image data to correlate to a portion of the first image data to re-register the second image frame to the first image frame, and of displaying a stabilized image display of the intravascular ultrasound blood vessel image, where the comparing step is done in orthogonal r-θ memory space.

According to another specific embodiment, the present invention provides an apparatus for an ultrasonic blood vessel imaging system. The apparatus includes a transducer for acquiring image data in polar r-θ coordinates from echoes from an intravascular target using ultrasounds to form an intravascular image, and a signal processing device capable of being coupled to the transducer and to a display for displaying the intravascular image. The apparatus also includes a computer-readable medium storing a computer-readable program. The computer-readable medium, which is coupled to be read by the signal processing device, is for comparing in orthogonal r-θ memory space, prior to scan conversion, a first image data of the intravascular target for a first image frame and a second image data of the intravascular target for a second image frame. The first and second image frames are successive. The computer-readable program determines the type and quantity of relative motion between the first image frame and the second image frame in order to provide a display of the intravascular image.

These and other embodiments of the present invention, as well as its advantages and features, are described in more detail in conjunction with the text below and attached figures.

DESCRIPTION OF THE SPECIFIC EMBODIMENTS

The present invention provides for the use in real space of a ring-shaped region of interest for image processing in intravascular ultrasound imaging systems that is more accurate than the use of the conventional rectangular region of interest, as explained below. Advantageously, the use of such a ring-shaped region of interest is consistent with the original image acquisition in polar coordinates and allows the retention of all acquired data samples for image stabilization processing analysis performed on the data samples prior to scan conversion. Accordingly, the image displayed on a display device is more accurate, because, unlike with conventional image processing, no originally acquired data is lost through interpolation. Further, the use of the ring-shaped region of interest in real space also enables the application of conventional image stabilization algorithms (e.g., correlation) in some embodiments with image processors used with intravascular ultrasound systems. Still further, pre-scan conversion image stabilization in accordance with embodiments of the present invention can also greatly enhance the effectiveness of other types of image processing (e.g., temporal frame filtering) that are typically performed pre-scan conversion, as discussed further below.

The present invention provides image processing methods which may be used in conjunction with the intravascular ultrasonic imaging system shown in FIG. 1, described in general above. In accordance with a specific embodiment of the present invention, a total of, for example, 256 spokes radially directed from the catheter 13 with 256 sample points per spoke is generally sufficient to obtain data to process the information. Of course, fewer or more spokes and/or sample points may be used in other embodiments. Further, signal processor 10 also includes a program memory 38 which may be used to store the computer-readable program(s) for implementing specific embodiment(s) of the present invention, as discussed further below. Alternatively, the computer-readable program(s) for implementing specific embodiments of the present invention may be stored on a memory coupled to signal processor 10. The memory may be, for example, a read-only memory, fixed disk drive, or removable disk drive.

Figure 2:
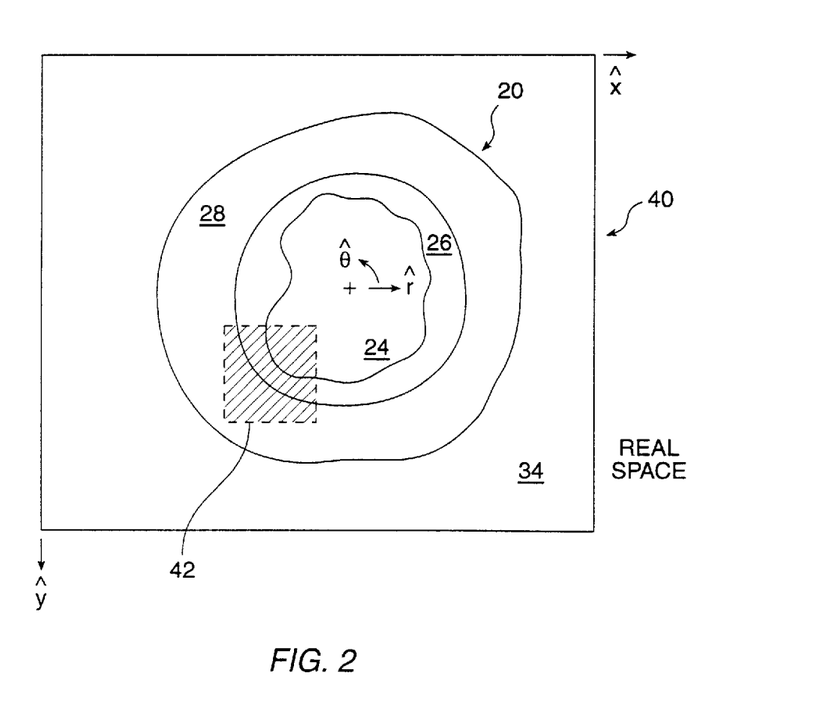
FIG. 2 is a representation of the cross-section of a blood vessel in rectangular coordinate "real space" to be displayed in an intravascular ultrasonic imaging system.
Figure 3:
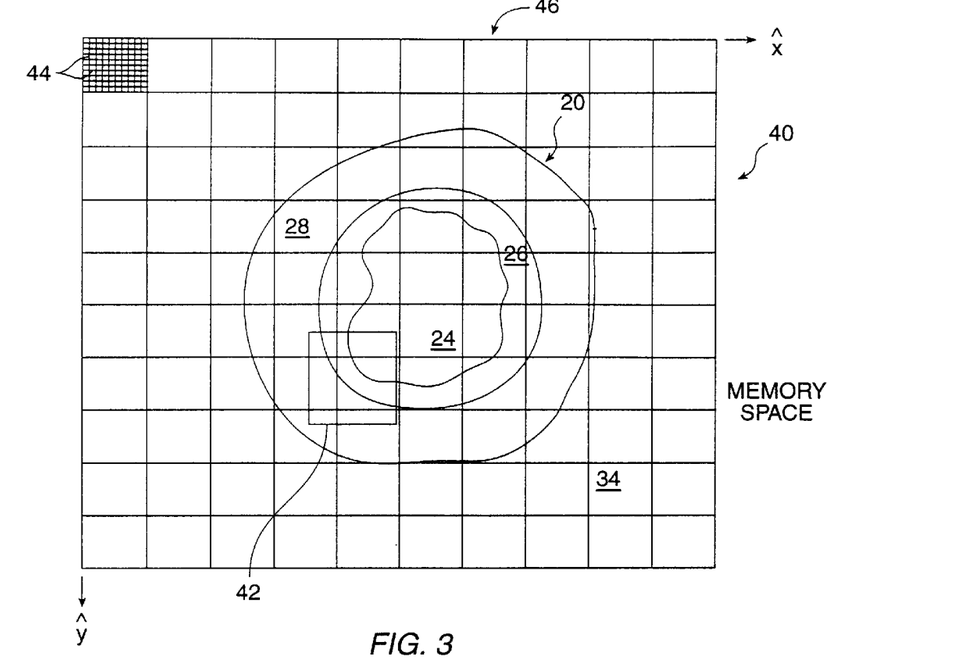
FIG. 3 is a representative image 40, in rectangular coordinate "memory space," of blood vessel 20, according to conventional image processors in ultrasonic imaging systems using a region of interest 42 which is rectangular in x-y coordinates, according to conventional image processing.

FIG. 2 is a representation of the cross-section of blood vessel 20 in rectangular x-y coordinate "real space" 19 to be displayed using an intravascular ultrasonic imaging system. As seen in FIG. 2, blood vessel 20 includes blood region 24, blood-wall interface or structure 26, and the vessel wall 28. Blood-wall interface or structure 26 may include, for example, plaque undesirably formed on the vessel wall 28. Region 34 represents indeterminate positions beyond vessel wall 28. As mentioned earlier, a conventional image processor in an IVUS imaging system acquires in polar coordinates the image data of blood vessel 20 shown in FIG. 2, performs scan conversion on the acquired data, and then stores the scan-converted image data 40 in rectangular x-y "memory space" shown in FIG. 3. FIG. 3 is a representative image 40 of blood vessel 20 in rectangular x-y coordinate memory space, according to a conventional image processor in an IVUS imaging system. Image 40 is obtained from a catheter located substantially at the center (as noted by the "+" shown in FIG. 2) of blood vessel 20. The conventional image processor uses a region of interest 42 which is rectangular in x-y coordinate memory space in order to perform image stabilization analysis. With the conventional image processor using the rectangular region of interest 42, the representation of the blood vessel 20 in real space (FIG. 2) substantially corresponds to the organization of the x-y rasterized image frame 40 (FIG. 3) stored in memory 32 of the signal processor 10. As seen in FIG. 3, the scan-converted x-y coordinate raster image data 40, which includes an array of pixels 44 (e.g., 220 pixels by 220 pixels; for simplicity FIG. 3 does not illustrate all the pixels, only some of which are shown in the upper left hand corner of the pixel array), is stored in the memory space of the display memory 32 in rectangular x-y coordinates and then analyzed for image stabilization purposes in that memory space. The search region 46 within which the smaller rectangular region of interest 42 is used for the image stabilization analysis (e.g., correlation) substantially corresponds to the "real space" of blood vessel 20 as displayed on display device 30 in rectangular x-y coordinates. Accordingly, the rectangular region of interest facilitates the use of known correlation techniques used for image stabilization, as discussed earlier. It is noted that the region of interest 42 in conventional image processing is "rectangular" both in the x-y memory space for the image stabilization analysis using, for example, correlation techniques, and in the real space. FIG. 2 illustrates this by showing the rectangular region of interest 42 (shown in dotted line and diagonally hatched) in real space that directly corresponds to the image data within rectangular region of interest 42 in x-y memory space (FIG. 3). With conventional image analysis, the region of interest 42 is rectangular in x-y memory space and corresponds to a rectangular region 48 in x-y real space due to the image stabilization analysis being performed on scan-converted x-y rasterized image data. As mentioned above, in the specific imaging environment in intravascular ultrasound systems, the conventional region of interest has therefore been rectangular (e.g., square), primarily because the various motions can be analyzed satisfactorily in rectangular (x, y) coordinates, albeit with inaccuracy due to acquired data loss from interpolations.

Figure 4:
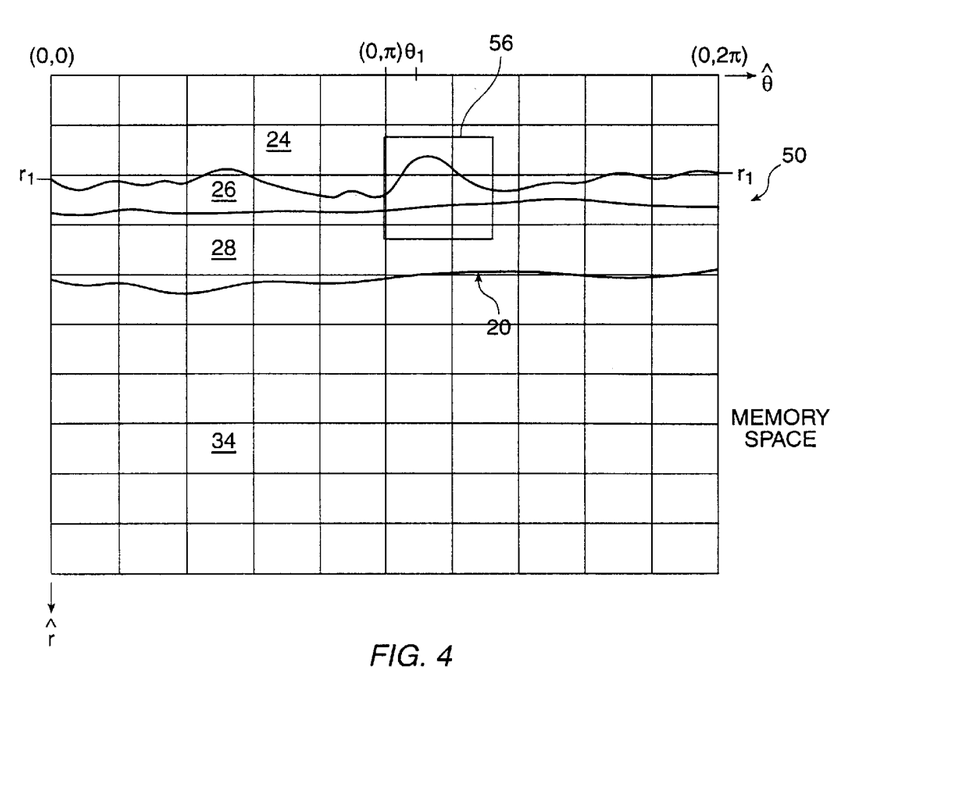
FIG. 4 is a representation of the cross-section of blood vessel 20 in rectangular r-θ coordinate memory space to be analyzed for motion and image stabilization analysis using an intravascular ultrasonic imaging system in accordance with the present invention.

In contrast, an image processor in accordance with the present invention acquires in polar coordinates the image data of blood vessel 20 shown in FIG. 2, stores the acquired data in orthogonal polar coordinate memory space for image motion analysis and/or stabilization in that memory space, and then performs scan conversion on the analyzed and/or stabilized image data for display. Unlike conventional image processors which utilize a rectangular region of interest in rectangular x-y coordinate memory space, an image processor according to the present invention utilizes a rectangular region of interest in orthogonal r-θ memory space. FIG. 4 is a representation of the cross-section of blood vessel 20 in orthogonal r-θ coordinate memory space to be analyzed for motion and/or image stabilization analysis using an intravascular ultrasonic imaging system in accordance with the present invention. Image data 50 is obtained from a catheter located substantially at the center (as noted by the "+" shown in FIG. 2) of blood vessel 20. As seen in FIG. 4, the pre-scan-converted r-θ coordinate image data 50 is stored in the orthogonal r-θ coordinates memory space of the display memory 32 and then analyzed for motion in that memory space. The r-θ coordinate image data 50 is the search region within which the smaller rectangular region of interest 52 is used for the image stabilization analysis (e.g., correlation). Accordingly, the rectangular region of interest facilitates the use of known correlation techniques used for image motion analysis and/or stabilization, as discussed earlier. Unlike with conventional image processing, in the present invention the rectangular region of interest 52 in r-θ coordinate memory space substantially corresponds to an annular or "ring-shaped" region in x-y coordinate real space, as discussed in more detail below. Because the present invention does not perform scan conversion on the acquired data until after motion and/or stabilization analysis of the image data is performed, more acquired data is retained and greater image accuracy is possible with the present invention. That is, motion is determined and/or stabilization techniques may be performed on the image data as originally acquired in polar coordinates, without the loss of information which would result from post-scan conversion interpolations performed by conventional image processing for the translation from polar coordinates to x-y coordinates. Thus, the complete image data in polar coordinate memory space is analyzed for motion and/or stabilization before being scan-converted to x-y raster image display. When pre-scan conversion image stabilization is performed in accordance with embodiments of the present invention, the effectiveness of image processing (e.g., temporal frame filtering, image averaging, or other methods) typically performed pre-scan conversion may be greatly enhanced, as will be discussed further below.

Figure 5:
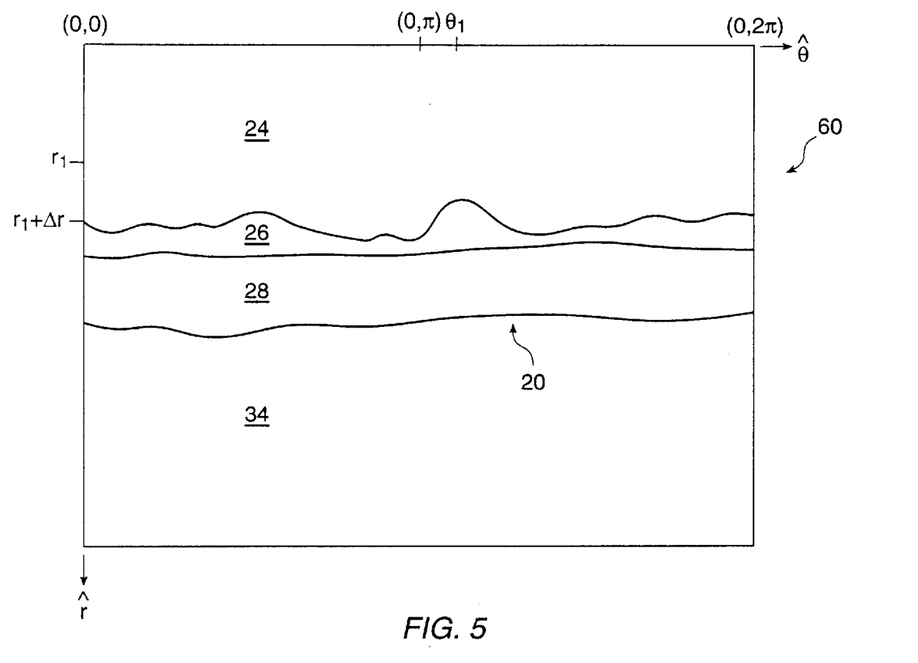
FIGS. 5 and 6 are simplified examples of possible successive image data 60 and 65, respectively, in orthogonal r-θ memory space that indicate pulsing and rotational motions, respectively, in relation to the intravascular image data 50 in orthogonal r-θ memory space shown in FIG. 4.
Figure 6:
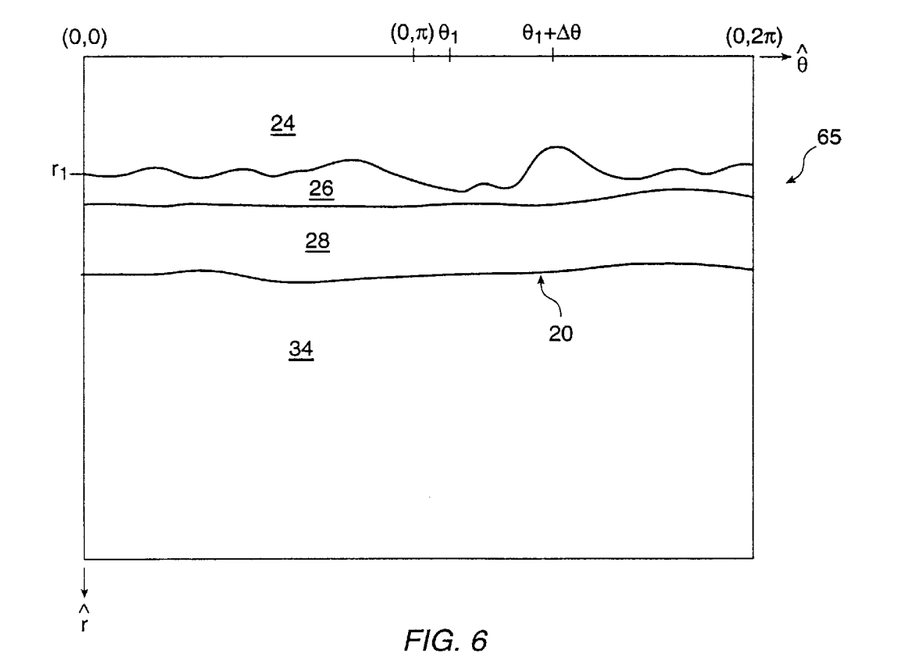

In providing accurate image display, the type and quantity of relative motion between the catheter and blood vessel 20 need to be determined so that the image may be re-registered accordingly and/or displayed accurately. In accordance with the present invention, the use of the region of interest which is rectangular in orthogonal r-θ memory space and ring-shaped in real space facilitates analysis in orthogonal r-θ memory space of the various types of motions encountered in IVUS systems. In accordance with the present invention, FIGS. 5 and 6 are simplified examples of possible successive image data 60 and 65, respectively, in orthogonal r-θ memory space that indicate pulsing and rotational motions, respectively, in relation to the intravascular image data 50 in orthogonal r-θ memory space shown in FIG. 4. In this example, the pulsating motion is determined to be dilation (in contrast to contraction), quantified by the difference Δr in location of a fixed point, e.g., on the blood-wall interface 26 at θ=0° from $r_1$, to ($r_1$, +Δr). Of course, it should be recognized that the contractive part of pulsation would be quantified by the difference in location Δr of a fixed point, e.g., on the blood-wall interface 26 at from $r_1$, to ($r_1$,−Δr).

As seen by comparing FIGS. 4 and 6, rotational motion of blood vessel 20 appears as a translation along the θ axis (variation along the θ axis for all values of r) in r-θ memory space. In the present example, the motion is determined to be a rotation in the positive θ direction, quantified by the difference Δθ in angular location of a fixed point, e.g., a protrusion on the blood-wall interface 26 from $θ_1$ to ($θ_1$+ Δθ). Of course, it should be recognized that rotational motion in the negative θ direction would be quantified by the difference Δθ in angular location of a fixed point e.g., the protrusion on the blood-wall interface 26 from $θ_1$ to ($θ_1$− Δθ).

Using, for example, conventional correlation techniques to compare the region of interest 56 (FIG. 4) with the image data 60 for pulsation (or the image data 65 for rotation), the motion analysis is thus easily performed for pulsation (or rotation) in orthogonal r-θ memory space. For pulsation, the pulsation may be displayed in the image accordingly. For rotation, the second image (FIG. 6) can also be adjusted or re-registered to the first image (FIG. 4) by the amount and direction indicated by the location in the search region of the correlation peak with the rectangular region of interest in r-θ memory space. The display of images is generally more accurate because the originally acquired r-θ image data is retained in entirety for use in the pre-scan conversion motion analysis without the loss of acquired image data due to the interpolations normally required for post-scan conversion motion analysis with conventional image processing.

Figure 7:
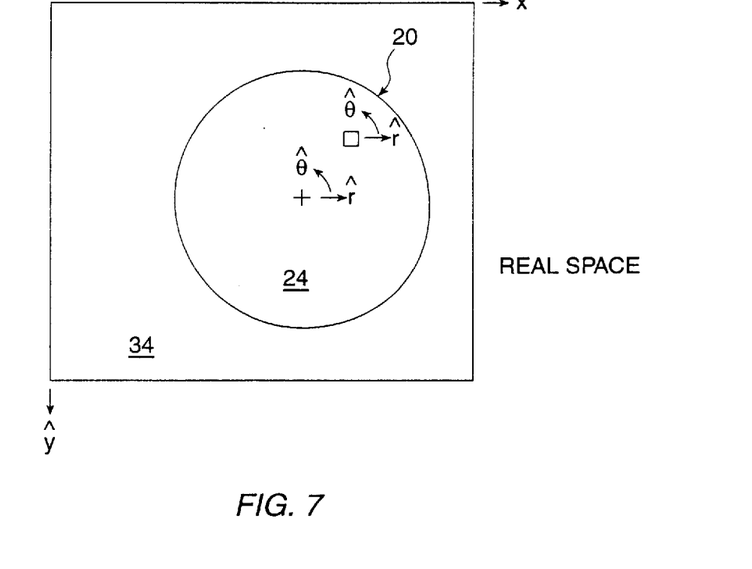
FIG. 7 is a simplified representation of blood vessel 20 in real space where the catheter has a first location substantially at the center (indicated by "+") of blood vessel 20 and a second location (indicated by "☐") within blood vessel 20 resulting from an in-plane translational motion, in accordance with the present invention.
Figure 8:
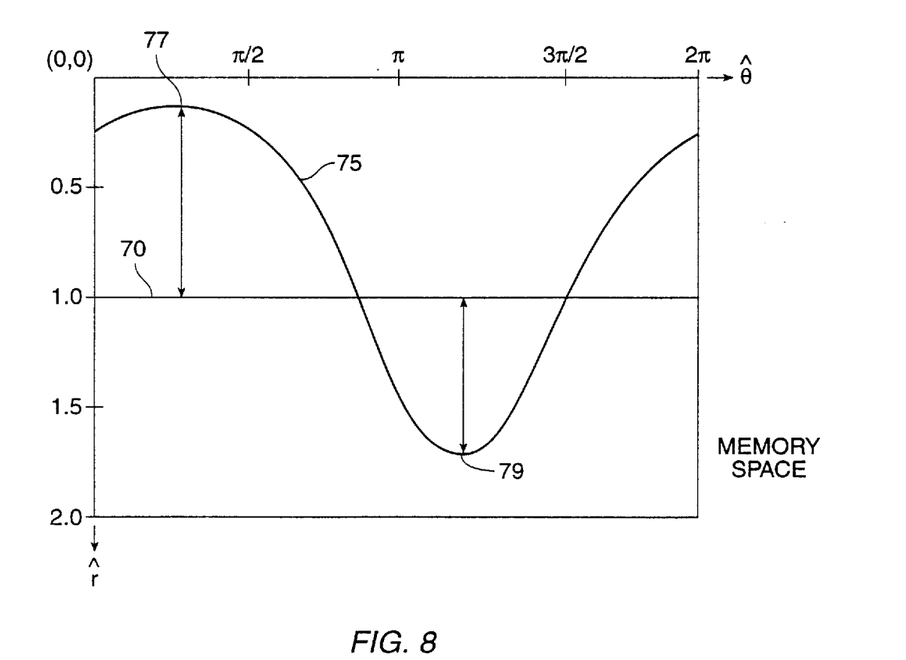
FIG. 8 is a simplified representation in orthogonal r-θ memory space of the image data 70 representing blood vessel 20 with the catheter located at the blood vessel center and, superimposed thereon, the image data 75 representing blood vessel 20 with catheter in the second location, in accordance with the present invention.

In accordance with the present invention, FIG. 7 is a simplified representation of blood vessel 20 in real space where the catheter has a first location substantially at the center (indicated by "+" in FIG. 7) of blood vessel 20 and a second location (indicated by "□" in FIG. 7) within blood vessel 20 resulting from an in-plane translational motion. For simplicity, blood vessel 20 in FIG. 7 has a radius from its center of 1. FIG. 8 is a simplified representation in orthogonal r-θ memory space of the image data 70 representing blood vessel 20 with the catheter located at the blood vessel center and, superimposed thereon, the image data 75 representing blood vessel 20 with catheter in the second location. It is noted that image data 70 is acquired in r-θ relative to the catheter in the first location, while image data 75 is obtained in r-θ relative to the catheter in the second location. Translational motion in accordance with the present invention is quantified by subtracting image data 70 and image data 75, and then determining the angle(s) and radial distance at which the maximum difference occurs between image data 70 and 75. For example, the maximum difference between image data 70 and 75 is about 0.8 at θ≈π/4 or about 45° (indicated by 77) with about 0.8 at θ≈5π/4 or about 225° (indicated by 79), in the example provided in FIG. 8. The translational motion which has occurred between the first and second locations of the catheter can be adjusted by re-registering the displayed image corresponding to image data 75 to the displayed image corresponding to image data 70 by a value of (r, θ) of about (0.8, 225°), or in reverse re-registering the displayed image corresponding to image data 70 by a value of (r, θ) of about (0.8, 225°) to the displayed image corresponding to image data 75.

It should be recognized that the motion analysis discussed above also generally applies to off-center catheter position or elliptically-shaped vessels. For an off-center catheter position, the image data representing a simplified blood vessel appears as a complex curve which is a periodic waveform, while the image data representing an elliptically-shaped blood vessel appears as a more complex curve. FIGS. 9A–9G are simplified illustrations of motion analysis provided by the present invention for a blood vessel with an off-center catheter position, and FIGS. 10A–10G are simplified illustrations of motion analysis provided by the present invention for an elliptically-shaped blood vessel.

Figure 9A:
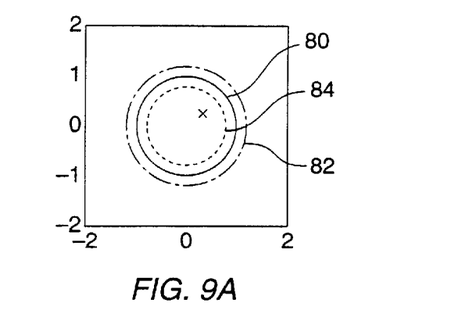
FIG. 9A is a simplified representation in real space of a circular cross-section of a blood vessel 80 with a catheter in an off-center position therein, superimposed with blood vessel 80 dilated (indicated by dashed-dotted line 82) and contracted (indicated by dotted line 84) in pulsation, in accordance with the present invention.
Figure 9B:
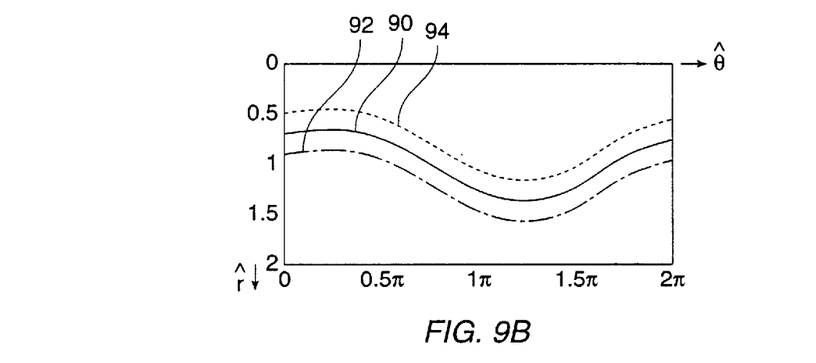
FIG. 9B is a simplified representation in orthogonal r-θ memory space of superimposed image data 90, 92 and 94 corresponding, respectively, to blood vessel 80 at-rest, dilated and contracted, in accordance with the present invention.

FIG. 9A is a simplified representation in real space of a circular cross-section of a blood vessel 80 with a catheter in an off-center position therein, superimposed with blood vessel 80 dilated (indicated by dashed-dotted line 82) and contracted (indicated by dotted line 84) in pulsation. For simplicity, blood vessel 80 has a radius from its center of 1. FIG. 9B is a simplified representation in orthogonal r-θ memory space of superimposed image data 90, 92 and 94 corresponding, respectively, to blood vessel 80 at-rest, dilated and contracted. It is noted that respective image data are acquired in r-θ relative to the particular position of the catheter. In this example, the pulsating motion is quantified by the differences in radial direction between image data 90 and 92 and between image data 90 and 94. The pulsating motion may thus be accurately displayed accordingly.

Figure 9C:
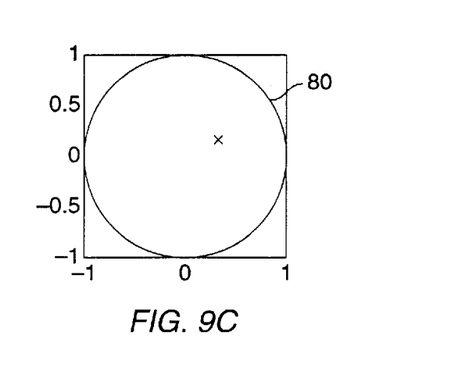
FIG. 9C is a simplified representation in real space of blood vessel 80 with a catheter in an off-center position therein, superimposed with blood vessel 80 in rotation, in accordance with the present invention.
Figure 9D:
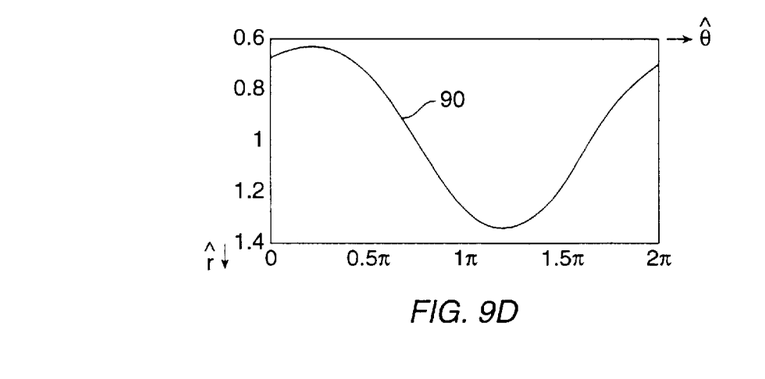
FIG. 9D is a simplified representation in orthogonal r-θ memory space of image data 90 corresponding to blood vessel 80 in rotation, in accordance with the present invention.

FIG. 9C is a simplified representation in real space of blood vessel 80 with a catheter in an off-center position therein, superimposed with blood vessel 80 in rotation. FIG. 9D is a simplified representation in orthogonal r-θ memory space of image data 90 corresponding to blood vessel 80 in rotation. The quantity of rotation may be determined by utilizing the rectangular region of interest within the larger search region to locate the relative position shift of a particular feature (not shown in FIGS. 9C or 9D, which are simplified representations) in image data 90, in a similar manner as discussed above for FIGS. 4 and 6 and as discussed below in a further example.

Figure 9E:
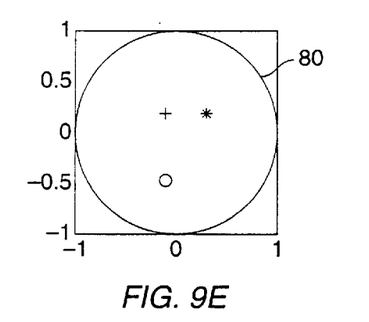
FIG. 9E is a simplified representation of blood vessel 80 in real space where the off-center catheter has a first location (indicated by "*") of blood vessel 80, a second location (indicated by "+"), and a third location (indicated by "○") from various types of in-plane translational motion, in accordance with the present invention.
Figure 9F:
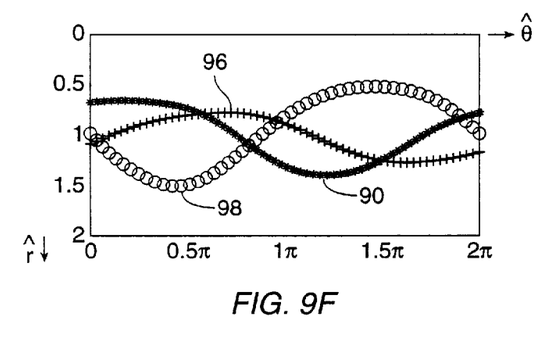
FIG. 9F is a simplified representation in orthogonal r-θ memory space of the superimposed image data 90 representing blood vessel 80 with the catheter located at the first location, image data 96 representing blood vessel 80 with the catheter located at the second position, and image data 98 representing blood vessel 80 with the catheter located at the third position, in accordance with the present invention.
Figure 9G:
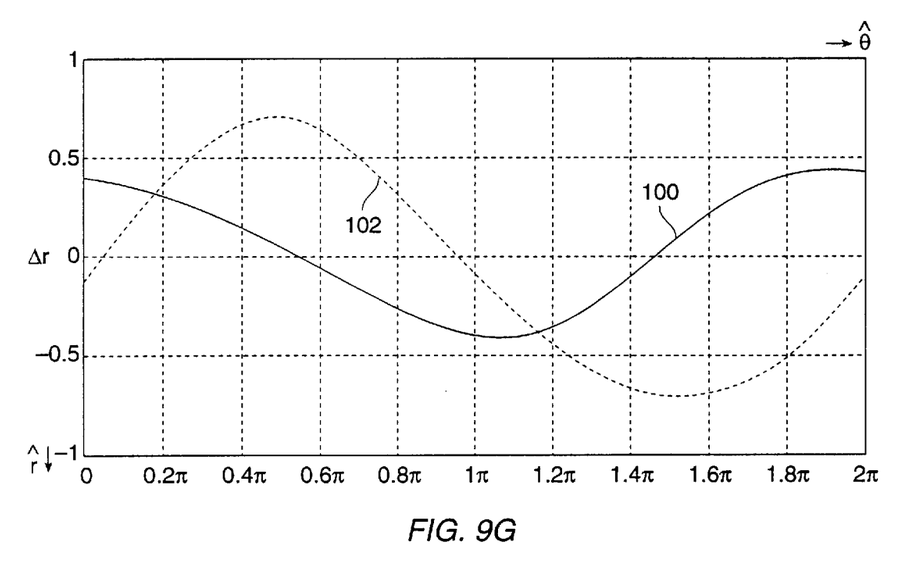
FIG. 9G is a simplified representation of the quantified translational motion between the first and second catheter locations and between the first and third catheter locations of FIG. 9E, in accordance with the present invention.

FIG. 9E is a simplified representation of blood vessel 80 in real space where the off-center catheter has a first location (indicated by "*" in FIG. 9E) of blood vessel 80, a second location (indicated by "+" in FIG. 9E), and a third location (indicated by "○" in FIG. 9E) from various types of in-plane translational motion. FIG. 9F is a simplified representation in orthogonal r-θ memory space of the superimposed image data 90 representing blood vessel 80 with the catheter located at the first location, image data 96 representing blood vessel 80 with the catheter located at the second position, and image data 98 representing blood vessel 80 with the catheter located at the third position. As discussed above, translational motion in accordance with the present invention is quantified by subtracting the image data corresponding to a particular catheter position and other image data corresponding to another catheter position, and then determining the angle(s) and radial distance at which the maximum difference occurs between compared image data for the two catheter positions. For example, the difference between image data 90 and 96 can be represented by a subtractive waveform 100 shown in FIG. 9G, which is a simplified representation of the quantified translational motion between the first and second catheter locations and between the first and third catheter locations of FIG. 9E. The angular location of these maxima/minima in the subtractive waveform indicates the angular direction the translation is occurring, with the absolute value of the amplitude of the maxima/minima providing the magnitude of the translation. Specifically, FIG. 9G indicates that the translation from the first location to the second location has a magnitude $\Delta r$ of about 0.4 and direction $\theta$ of about $\pi$ or 180° or about $2\pi$ or 0° or 360°. As another example, the difference between image data 90 and 98 can be represented by a subtractive waveform 102 shown in FIG. 9G. FIG. 9G also indicates that the translation from the first location to the third location has a magnitude $\Delta r$ of about 0.7 and direction $\theta$ of about $\pi/2$ or 90° or about $3\pi/2$ or 270°. Similarly, the difference between image data 96 and 98 could also have been shown in FIG. 9G. In order to compare image data from one catheter position with image data from another catheter position in the orthogonal r-$\theta$ memory space, multiple rectangular regions of interest in the image data may be used to span the entire range of $\theta$ in the larger search region to determine the type and quantity of in-plane translation. For example, the regions of interest may span the entire range $\theta$ of the search region in order to determine the angular location of the maximum difference between the image data for the different catheter positions. In contrast, comparing image data from one catheter position with image data from another catheter position in the orthogonal r-$\theta$ memory space, a single rectangular region of interest in the image data may be used in the larger search region without spanning the entire range of $\theta$ to determine the type and quantity of rotation or pulsation.

Figure 10A:
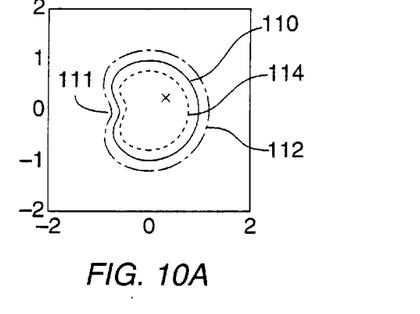
FIG. 10A is a simplified representation in real space of an elliptically-shaped circular cross-section of a blood vessel 110 with a catheter in an off-center position therein, superimposed with blood vessel 110 dilated (indicated by dashed-dotted line 112) and contracted (indicated by dotted line 114) in pulsation, in accordance with the present invention.
Figure 10B:
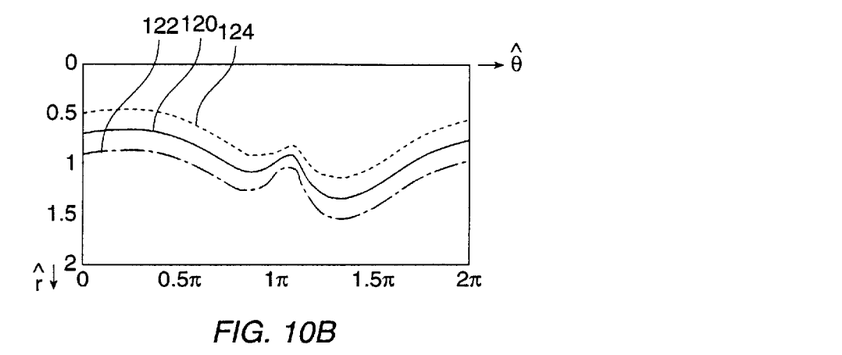
FIG. 10B is a simplified representation in orthogonal r-θ memory space of superimposed image data 120, 122 and 124 corresponding, respectively, to blood vessel 110 at-rest, dilated and contracted, in accordance with the present invention.

To further illustrate the present invention, FIGS. 10A–10F are simplified illustrations of motion analysis provided by the present invention for an elliptically-shaped blood vessel. It is noted that the elliptical shape of the blood vessel may be due to a distinct feature, such as plaque, formed on the blood vessel wall. FIG. 10A is a simplified representation in real space of an elliptically-shaped circular cross-section of a blood vessel 110 with a catheter in an off-center position therein, superimposed with blood vessel 110 dilated (indicated by dashed-dotted line 112) and contracted (indicated by dotted line 114) in pulsation. For simplicity, blood vessel 110 has a maximum radius from its center of about 1 and a feature 111 on the wall of vessel 110 which has a radius from the center of less than the maximum radius. FIG. 10B is a simplified representation in orthogonal r-$\theta$ memory space of superimposed image data 120, 122 and 124 corresponding, respectively, to blood vessel 110 at-rest, dilated and contracted. The respective image data are acquired in r-$\theta$ relative to the particular position of the catheter. In this example, the pulsating motion is quantified by the differences in radial direction between image data 120 and 122 and between image data 120 and 124. Each image data (120, 122 or 124) reflects the presence of feature 111 in vessel 110. By re-registering a successive image frame by the distance $\Delta r$ between successive image data, the displayed image may be stabilized and show the pulsating motion.

Figure 10C:
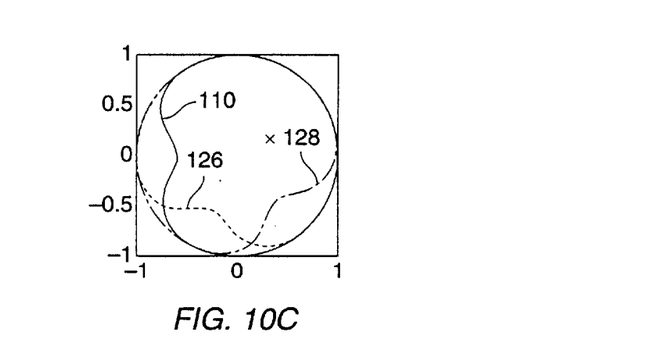
FIG. 10C is a simplified representation in real space of blood vessel 110 with a catheter in an off-center position therein, superimposed with simplified representations of blood vessel 110 rotated by different values of θ (indicated by dotted-line 126, and indicated by dashed-dotted line 128) in a positive direction, in accordance with the present invention.
Figure 10D:
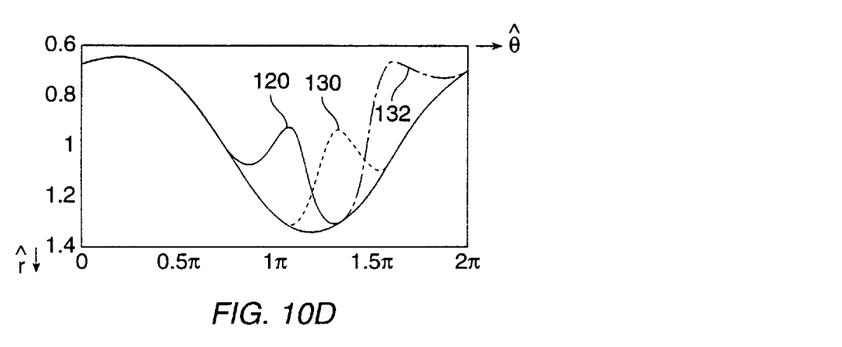
FIG. 10D is a simplified representation in orthogonal r-θ memory space of image data 120, 130 and 132, respectively, corresponding to blood vessel 110 in rotation, in accordance with the present invention.

FIG. 10C is a simplified representation in real space of blood vessel 110 with a catheter in an off-center position therein, superimposed with simplified representations of blood vessel 110 rotated by different values of $\theta$ (indicated by dotted-line 126, and indicated by dashed-dotted line 128) in a positive direction. FIG. 10D is a simplified representation in orthogonal r-$\theta$ memory space of image data 120, 130 and 132, respectively, corresponding to blood vessel 110 in rotation. The quantity of rotation may be determined by utilizing the rectangular region of interest within the larger search region to locate the relative position shift associated with a particular feature (such as feature 111 shown in FIGS. 10C) in image data 120, 130 and 132, in a similar manner as discussed above for FIGS. 4 and 6. As seen in FIG. 10D, image data 130 has a peak (associated with feature 111) which is located about $\pi/4$ or 45° relative to the peak in image data 120, indicating that blood vessel 110 has rotated by $\pi/4$ or 45° from its at-rest position. Further, as seen in FIG. 10D, image data 132 has a peak (associated with feature 111) which is located about $\pi/2$ or 90° relative to the peak in image data 120, indicating that blood vessel 110 has rotated by $\pi/2$ or 90° from its at-rest position.

Figure 10E:
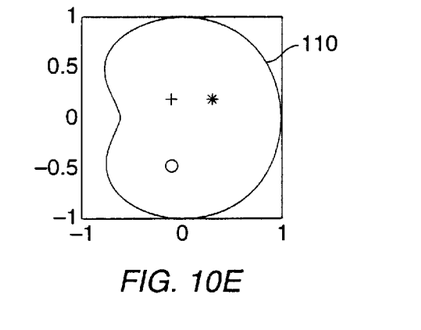
FIG. 10E is a simplified representation of blood vessel 110 in real space where the off-center catheter has a first location (indicated by "*") of blood vessel 110, a second location (indicated by "+"), and a third location (indicated by "○") from various types of in-plane translational motion, in accordance with the present invention.
Figure 10F:
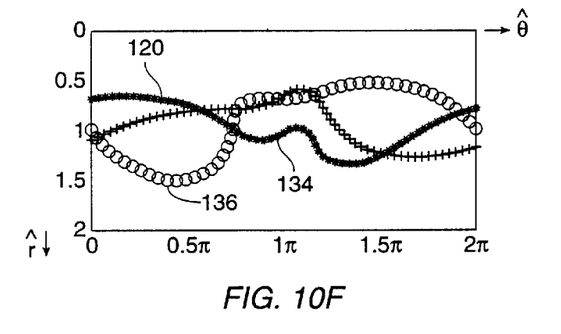
FIG. 10F is a simplified representation in orthogonal r-θ memory space of the superimposed image data 120 representing blood vessel 110 with the catheter located at the first location, image data 134 representing blood vessel 110 with the catheter located at the second position, and image data 136 representing blood vessel 110 with the catheter located at the third position, in accordance with the present invention.
Figure 10G:
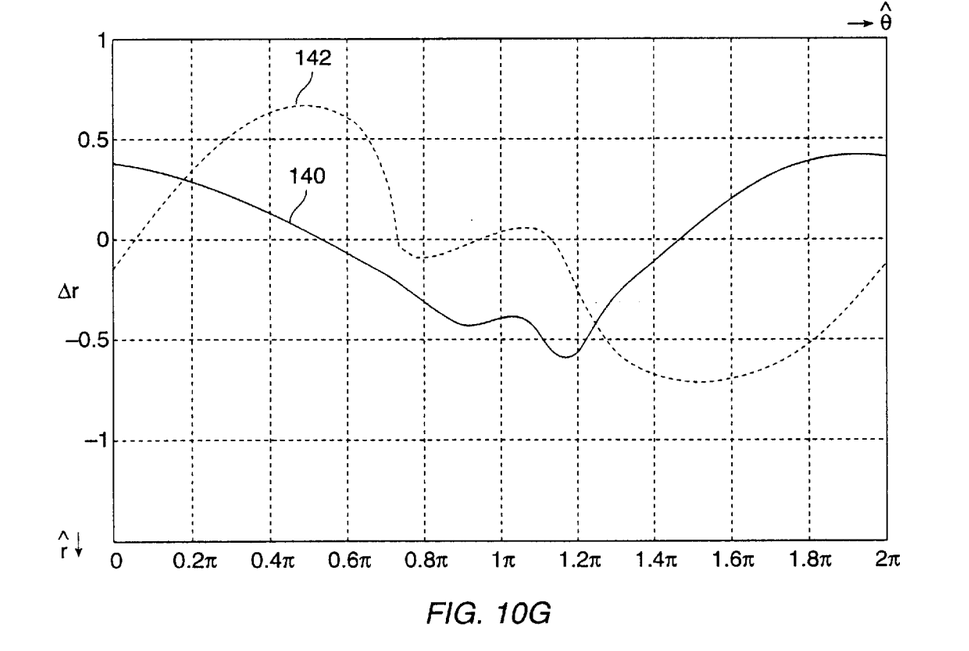
FIG. 10G is a simplified representation of the quantified translational motion between the first and second catheter locations and between the first and third catheter locations of FIG. 10E, in accordance with the present invention.

FIG. 10E is a simplified representation of blood vessel 110 in real space where the off-center catheter has a first location (indicated by "*" in FIG. 10E) of blood vessel 110, a second location (indicated by "+" in FIG. 10E), and a third location (indicated by "○" in FIG. 10E) from various types of in-plane translational motion. FIG. 10F is a simplified representation in orthogonal r-$\theta$ memory space of the superimposed image data 120 representing blood vessel 110 with the catheter located at the first location, image data 134 representing blood vessel 110 with the catheter located at the second position, and image data 136 representing blood vessel 110 with the catheter located at the third position. As discussed above, translational motion in accordance with the present invention is quantified by subtracting the image data corresponding to a particular catheter position and other image data corresponding to another catheter position, and then determining the angle(s) and radial distance at which the maximum difference occurs between compared image data for the two catheter positions. For example, the difference between image data 120 and 134 can be represented by a subtractive waveform 140 shown in FIG. 10G, which is a simplified representation of the quantified translational motion between the first and second catheter locations and between the first and third catheter locations of FIG. 10E. The angular location of these maxima/minima in the subtractive waveform indicates the angular direction the translation is occurring, with the absolute value of the amplitude of the maxima/minima providing the magnitude of the translation. Specifically, FIG. 10G indicates that the translation from the first location to the second location has a magnitude $\Delta r$ of about 0.4 and direction $\theta$ of about 0° or about $2\pi$ or 360°. As another example, the difference between image data 120 and 136 can be represented by a subtractive waveform 142 shown in FIG. 10G. FIG. 10G indicates that the translation from the first location to the third location has a magnitude $\Delta r$ of about 0.7 and direction $\theta$ of about $\pi/2$ or 90° or about $3\pi/2$ or 270°. Similarly, the difference between image data 134 and 136 could also have been shown in FIG. 10G.

As mentioned above, other image processing techniques that are typically used post scan-conversion in conventional IVUS systems using post-scan conversion image stabilization in x-y memory space may be greatly enhanced when used with embodiments of the present invention which utilize pre-scan conversion image stabilization in r-$\theta$ memory space. For example, such image processing techniques include temporal frame filtering in the r-$\theta$ domain (such as described in more detail in U.S. Pat. No. 5,476,096, which is hereby incorporated by reference for all purposes) or other techniques. In order to demonstrate the enhanced effectiveness of image processing techniques with the use of embodiments of the present invention, temporal frame filtering is discussed as an example of such an image processing technique. Temporal frame filtering involves looking at successive (in time) image frames in the r-θ domain and enhancing the image by determining from a large change between the image data in successive frames that there is noise in the image, or by determining from a slight change that there is a tissue (or image) edge in the vascular image. It is noted that when conventional IVUS systems perform post-scan conversion image stabilization in the x-y domain, the effectiveness of temporal frame filtering for discerning the difference between a noisy image or an image edge is limited when vascular motion is encountered. In particular, the vascular motion makes it difficult to determine whether the change in the image data in successive frames is from noise, vascular motion, or an image edge, and the accuracy of the displayed image may be questionable although the displayed image may appear stable. With embodiments of the present invention that use pre-scan conversion image stabilization in r-θ memory space, there is much less uncertainty in determining whether a change in the image data in successive frames is from noise, vascular motion or an image edge, because vascular motion has already been accounted for prior to scan-conversion and use of the temporal frame filtering or other image processing technique. With the use of embodiments of the present invention, the algorithms used in temporal frame filtering can be made more aggressive or extreme in determining the difference between noise and an image edge due to the changes in image data in successive frames. Accordingly, the accuracy of the displayed image that has been temporal frame filtered is more certain in addition to the displayed image being stable due to the application of pre-scan conversion image stabilization in the r-θ domain. It should be recognized that other image processing techniques, in addition to temporal frame filtering, that are typically performed on post-scan conversion stabilized images also would benefit from the pre-scan conversion stabilization according to embodiments of the present invention.

The use of a region of interest that is ring-shaped in real space and rectangular in orthogonal r-θ coordinate memory space facilitates the accurate and efficient analysis of various motions in polar coordinates, thereby resulting in a more accurate and/or stable image display. Further, memory requirements and related hardware requirements for such image processors using pre-scan conversion image stabilization according to the present invention are much less than the memory and hardware requirements for conventional image processors using post-scan conversion image stabilization in order to display the same image frame of, for example, 256×256 samples of image data acquired in r-θ (e.g., 256 radial spokes with 256 data or sample points per spoke). Specifically, embodiments of the present invention using pre-scan conversion image stabilization in the r-θ domain have a much lower data density (e.g., 256×256 pixel data in r-θ memory space) in comparison to the higher data density (e.g., 512×512 pixel data or 1024×1024 pixel data in x-y memory space) of conventional systems using post-scan conversion image stabilization in the x-y domain for a given image frame of 256×256 samples. Therefore, embodiments of the present invention would utilize about 1/16th megabyte (MB) of memory in r-θ memory space for the pre-scan converted 256×256 image frame; whereas, conventional systems having 512×512 pixel data in x-y memory space would require about 1/4th MB of memory for the post-scan converted image frame and conventional systems having 1024×1024 pixel data in x-y memory space would require about 1 MB of memory for the post-scan converted image frame. In addition, embodiments of the present invention could also utilize less complex and/or cheaper hardware (e.g., running at slower clock speeds, handling smaller amounts of data, etc.) for implementation in comparison with conventional systems utilizing post-scan conversion image stabilization for such high data densities.

While the invention has been particularly shown and described with reference to preferred embodiments thereof, it will be understood by those skilled in the art that the foregoing and other changes in the form and details may be made therein without departing from the spirit or scope of the invention. As an example, the origin of the r-θ orthogonal axes in memory space may be differently located than shown in FIGS. 4–10 without departing from the present invention. As another example, although the specific embodiments discussed utilize conventional correlation algorithms, other specific embodiments may utilize analog or optical comparison techniques to compare success image data. It is therefore not intended that this invention be limited, except as indicated by the appended claims.

What is claimed is:

1. A method of determining relative motion between successive intravascular ultrasound blood vessel images, said method comprising the steps of:

illuminating an intravascular target with ultrasonic energy from within the intravascular target to generate ultrasonic echoes from the intravascular target;

transforming the ultrasonic echoes from the intravascular target into a received signal to acquire first image data in polar r-θ coordinates for a first image frame of an intravascular ultrasound blood vessel image and second image data in polar r-θ coordinates for a second image frame of the intravascular ultrasound blood vessel image, said second image frame and said first image frame being successive image frames; and comparing, prior to scan conversion, said first image data and said second image data to determine the type and quantity of relative motion from said first image frame to said second image frame.

2. The method of claim 1 further comprising the steps of:

performing, prior to scan conversion, an image stabilization analysis between said second image data and said first image data in orthogonal r-θ memory space by using a rectangular region of interest in said second image data to correlate to a portion of said first image data to re-register said second image frame to said first image frame; and displaying a stabilized image display of said intravascular ultrasound blood vessel image; and wherein said comparing step is done in said orthogonal r-θ memory space.

3. The method of claim 2 further comprising the step of:

performing, prior to scan conversion, temporal frame filtering in said orthogonal r-θ memory space.

4. The method of claim 1 wherein said first image frame and said second image frame are successive slices of intravascular regions, said slices comprising a plurality of radial vectors from an intravascular ultrasound imaging system.

5. The method of claim 1 wherein said first image data and said second image data are acquired as digital information stored in said orthogonal r-θ memory space.

6. The method of claim 1 wherein said comparing step determines relative motion from said first image frame to said second image frame, said relative motion being selected from pulsation, rotation, in-plane translation, and combinations thereof.

7. The method of claim 6 wherein a change only in radial magnitude for a range of θ from said first image data to said second image data indicates pulsation.

8. The method of claim 7 wherein said change being negative indicates contraction and said change being positive indicates dilation.

9. The method of claim 6 wherein a change only in θ for a range of distance r from said first image data to said second image data indicates rotation.

10. The method of claim 6 wherein a maximum difference in radial magnitude from said first image data to said second image data occurs at a particular θ, and said maximum difference indicates the magnitude of in-plane translation and said particular θ indicates the direction of said in-plane translation.

11. Apparatus for an ultrasonic blood vessel imaging system comprising:

a transducer for acquiring image data in polar r-θ coordinates from echoes from an intravascular target using ultrasounds generated from within the intravascular target to form an intravascular image;

a signal processing device capable of being coupled to said transducer and to a display for displaying said intravascular image;

a computer-readable medium storing a computer-readable program, said computer-readable medium coupled to be read by said signal processing device, said computer-readable program for comparing in orthogonal r-θ memory space, prior to scan conversion, a first image data of said intravascular target for a first image frame and a second image data of said intravascular target for a second image frame, said first and second image frames being successive, wherein said computer-readable program determines the type and quantity of relative motion between said first image frame and said second image frame in order to provide a display of said intravascular image.

12. The apparatus of claim 11 wherein said computer-readable program is able to determine said relative motion, said relative motion being selected from rotation, pulsation, in-plane translation, and combinations thereof.

13. The apparatus of claim 12 wherein said computer-readable program further performing, prior to scan conversion, an image stabilization analysis between said second image data and said first image data in orthogonal r-θ memory space by using a rectangular region of interest in said second image data to correlate to a portion of said first image data to re-register said second image frame to said first image frame.

14. The apparatus of claim 13 wherein said computer-readable program further performs, prior to scan conversion, temporal frame filtering in said orthogonal r-θ memory space.

15. The apparatus of claim 12 wherein said computer-readable program is able to determine said relative motion to be pulsation if there is a change only in radial magnitude for a range of θ from said first image data to said second image data.

16. The apparatus of claim 15 wherein said computer-readable program is determine said pulsation as contractive when said change is negative and as dilative when said change is positive.

17. The apparatus of claim 12 wherein said computer-readable program is able to determine said relative motion to be rotation if there is a change only in θ for a range of distance r from said first image data to said second image data.

18. The apparatus of claim 12 wherein said computer-readable program is able to determine said relative motion to be in-plane translation if there is a maximum difference in radial magnitude from said first image data to said second image data occurring at a particular θ, and said computer-readable program determines said maximum difference to indicate the magnitude of in-plane translation and said particular θ to indicate the direction of said in-plane translation.

19. The apparatus of claim 12 wherein said computer-readable program is able to determine relative motion from said first and said second image frames when said motion is caused by motion of said transducer within said blood vessel.

20. The apparatus of claim 12 wherein said computer-readable program is able to determine said relative motion from said first and said second image frames when said motion is caused by motion of said blood vessel.

21. The apparatus of claim 12 wherein said first and said apparatus acquires second image data as digital information.

22. The apparatus of claim 12 wherein said first and said apparatus originally acquires second image data as analog information, and wherein said apparatus further comprises an analog-to-digital converter for converting said analog information into digital information.

* * * * *